United States Patent [19]

Ogasawara

[11] Patent Number: 4,965,048
[45] Date of Patent: Oct. 23, 1990

[54] THIN-LAYER CHROMATOGRAPHY FLAME IONIZATION DETECTOR FOR QUANTITATIVE ANALYSIS OF CHROMATOGRAPHICALLY-SEPARATED SUBSTANCES

[75] Inventor: Minoru Ogasawara, Tokyo, Japan

[73] Assignee: Iatron Laboratories, Inc., Tokyo, Japan

[21] Appl. No.: 412,629

[22] Filed: Sep. 25, 1989

Related U.S. Application Data

[63] Continuation of Ser. No. 120,348, Nov. 13, 1987, abandoned.

[30] Foreign Application Priority Data

Apr. 13, 1987 [JP] Japan .................................. 62-088702

[51] Int. Cl.$^5$ ............................................. G01N 21/72
[52] U.S. Cl. ........................................ 422/54; 436/154
[58] Field of Search .................. 422/54; 436/154, 171; 250/389, 382; 340/579

[56] References Cited

U.S. PATENT DOCUMENTS

| | | | |
|---|---|---|---|
| 3,615,237 | 10/1971 | Speakman | 436/154 |
| 3,744,973 | 7/1973 | Dubsky | 422/54 |
| 3,814,583 | 6/1974 | Miller | 422/54 |
| 4,182,740 | 1/1980 | Hartman et al. | 422/54 |
| 4,273,559 | 6/1981 | Nelson | 422/54 |
| 4,508,685 | 4/1985 | Sisti | 422/54 |

FOREIGN PATENT DOCUMENTS

| | | |
|---|---|---|
| 0198593 | 10/1986 | European Pat. Off. . |
| 50-158 | 1/1975 | Japan . |
| 61-19764 | 2/1986 | Japan . |
| 1225239 | 3/1971 | United Kingdom . |

Primary Examiner—Kenneth M. Schor
Attorney, Agent, or Firm—Michael N. Meller

[57] ABSTRACT

A flame ionization detector is used for carrying out a quantitative analysis of chromatographically-separated substances in thin-layer chromatography. The detector comprises a gas burner for forming a hydrogen flame. A thin-layer chromatographic element or a rod-like element which carries the chromatographically-separated substances is passed through the hydrogen flame so that the separated substances are burned and ionized. The detector further comprises an electrode which is disposed above the hydrogen flame and exposed to the ionized gas generated by the burning of the separated substances. A voltage is applied between the gas burner and the electrode so that the former is given a positive polarity and the latter a negative polarity. An electric current which is caused by the exposure of the negative electrode to the ionized gas is detected and amplified. A third electrode is disposed to surround the negative electrode so that an amount of each of the separated substances can be proportioned to the amplified output value thereof.

4 Claims, 7 Drawing Sheets

*PRIOR ART*

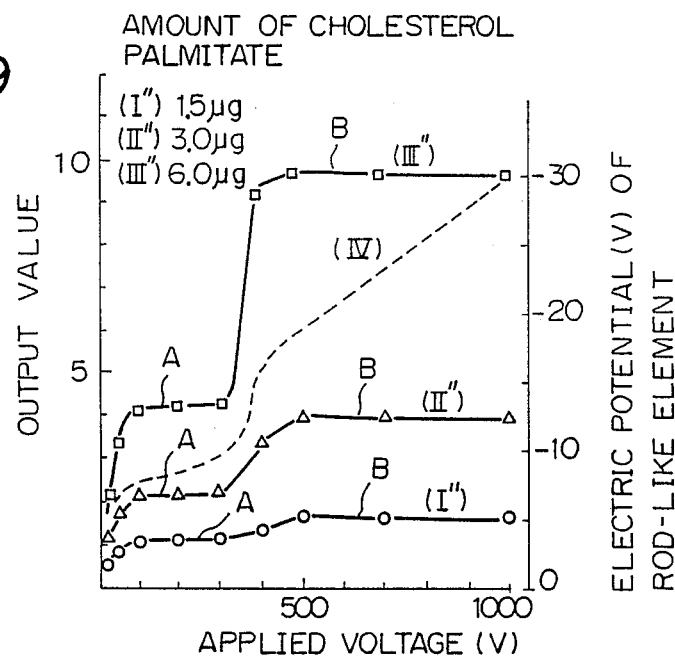
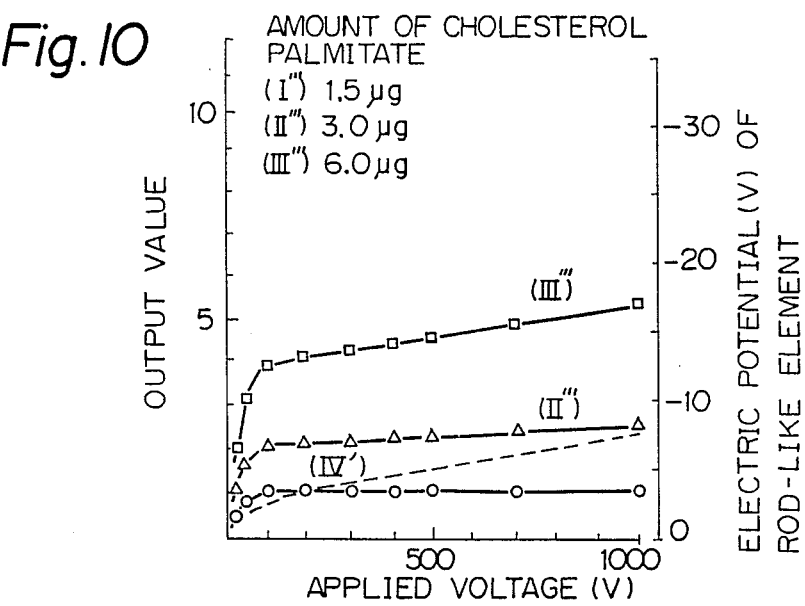

PRIOR ART

THIN-LAYER CHROMATOGRAPHY FLAME IONIZATION DETECTOR FOR QUANTITATIVE ANALYSIS OF CHROMATOGRAPHICALLY-SEPARATED SUBSTANCES

This is a continuation of Ser. No. 120,348, filed 11-13-87, and now abandoned.

BACKGROUND OF THE INVENTION (1) Field of the Invention

The present invention relates to a thin-layer chromatography flame ionization detector for carrying out a quantitative analysis of chromatographically-separated substances obtained from a sample solution in a thin-layer chromatography system.

(2) Description of the Related Art

In the field of chromatography, the use of a flame ionization detector (FID) for carrying out a quantitative analysis of chromatographically-separated substances obtained from a sample of a mixture in chromatography systems is well known.

For example, a flame ionization detector used in the field of gas chromatography comprises a gas burner connected to a hydrogen gas source and to a chromatographic column through which a sample of mixed gas is passed, a collector electrode disposed above a hydrogen flame formed by the nozzle of the hydrogen gas burner, an electric source for applying a voltage between the hydrogen gas burner and the collector electrode, an amplifier for detecting and amplifying an electric current generated at the collector electrode, and a recorder connected to the amplifier for recording an output obtained therefrom as a chromatogram.

In operation, the sample gas is passed through the chromatographic column in such a manner that it is chromatographically separated into at least two kinds of gaseous substances, of which the sample gas is composed. The separated substances, which are successively fed out of the chromatographic column, are fed into the hydrogen ga burner and are mixed with hydrogen gas fed therein from the hydrogen gas source. Thus, the separated substances are successively ejected together with hydrogen gas from a nozzle port of the hydrogen gas burner, and are burned and ionized by the hydrogen flame formed by the nozzle port of the hydrogen gas burner. A voltage is applied between the collector electrode and the hydrogen gas burner by the electric source and the collector electrode is exposed to the burned and ionized gas so that an ionization current is generated at the collector electrode. The ionization current is detected and amplified by the amplifier and is then recorded as a chromatogram by the recorder.

The value of the ionization current generated in the collector electrode on each of the separated substances depends upon the amount of ionized gas obtained by the burning of the corresponding one of the separated substances. In other words, the amount of each of the separated substances corresponds to an output value obtained from the amplifier at the corresponding one of the separated substances. This makes it possible for the separated substances to be quantitatively analyzed by using a calibration characteristic representing a relationship between a known amount of each of the separated substances and an output value obtained from the amplifier at the known thereof.

In the flame ionization detector used in the field of gas chromatography, since the calibration characteristic representing a relationship between an amount of each of the separated substances and an output value obtained from the amplifier thereat can be obtained as a linear function, it is possible to carry out an accurate quantitative analysis with a good reproducibility.

In the field of thin-layer chromatography, also it is known that a flame ionization detector can be used for a quantitative analysis of chromatographically-separated substances obtained from a sample solution in a thin-layer chromatography system. This thin-layer chromatography flame ionization detector is similar in essence to that used in the field of gas chromatography.

In the thin-layer chromatography system concerned, a thin-layer chromatographic element is used, as disclosed in Examined Japanese Patent Publication No. 52-35320 (Patent No. 907248), which forms a part of a thin-layer chromatograph. The thin-layer chromatographic element comprises a rod having a diameter of about 0.8 to 1.0 mm and made of a refractory material such as silica glass, and a thin-layer formed on the rod by coating the surface thereof with an inorganic absorbent material such as silica gel, alumina, diatomite or the like. A sample solution is spotted on the rod-like element or the thin-layer chromatographic element and is then developed along a length of the rod-like element with a developing solvent, in the same manner as used in a known thin-layer chromatography system, whereby the sample solution is chromatographically separated into at least two kinds of substances, which appear to form at least two zone sections on the rod-like element.

In the operation of the thin-layer chromatography flame ionization detector, the rod-like element carrying the developed and separated substances is gradually passed through the hydrogen flame formed by the hydrogen gas burner, so that these substances are burned and ionized thereby. Thus, the collector electrode is exposed to the burned and ionized gas so that an ionization current is generated at the collector electrode. The ionization current is detected and amplified by the amplifier and is then recorded as a chromatogram by the recorder. Namely, in the flame ionization detector used in the field of thin-layer chromatography, a quantitative analysis of each of the separated substances can be also carried out in substantially the same manner as that used in the field of gas chromatography.

In the thin-layer chromatography flame ionization detector, it is also necessary to prepare a calibration characteristic representing a relationship between an amount of each of the separated substances and an output value obtained from the amplifier on the amount thereof, before carrying out a quantitative analysis of the separated substances, but it is impossible to obtain such a calibration characteristic as a linear function In other words, the calibration characteristic is similar to an exponential function, and accordingly, the thin-layer chromatography flame ionization detector possesses various drawbacks, and little attempt has been made to overcome these drawbacks.

This is because, first, it is very difficult to obtain calibration characteristics on substances to be chromatographically separated, since many plots must be prepared to obtain each calibration characteristic due to the curving thereof. In other words, in order to obtain the calibration characteristics, it is necessary to seek output values of the amplifier which correspond to many kinds of known amounts of each of the substances, because the calibration characteristic so obtained is not linear but curved.

As another drawback, it is impossible to expect a uniform precision in a quantitative analysis of chromatographically-separated substances because of an uneven, therefore, nonuniform gradient of the calibration characteristic curves.

Furthermore, it is very difficult to carry out a reliable quantitative analysis of chromatographically-separated substances because of the distinctiveness of the calibration characteristic curves. In particular, a quantitative analysis of chromatographically-separated substances is frequently carried out in such a manner that each of the separated substances is quantitatively evaluated from the calibration characteristic curve thereof not as an absolute amount but as a relative amount, as in other quantitative analysis fields. In this case, the ratios among the output values of the amplifier which correspond to the separated substances, respectively, are quantitatively evaluated as a relative amount, but these ratios are affected by the amount of a sample solution spotted on the thin-layer chromatographic element, because of the distinctiveness of the calibration characteristic curves. In other words, it is necessary to spot the same amount of a sample solution at all times on the rod-like element, to obtain a reliable quantitative evaluation of the separated substances. However, since it is very difficult or substantially impossible to spot exactly the same amount of a sample solution at all times on the rod-like element, the reproducibility of the quantitative analysis, wherein the chromatographically-separated substances are quantitatively evaluated as a relative amount, are poor.

Namely, in the prior flame ionization detector used in the field of thin-layer chromatography, an accurate quantitative analysis cannot be carried out with a good reproducibility because of the non-linearity of the calibration characteristics.

According to the research by the inventor, it can be assumed that the non-linearity of the calibration characteristics occurs for the following reasons:

When the rod-like element carrying the chromatographically-separated substances is passed through the hydrogen flame, the element is charged with electricity in accordance with an electric potential distribution between the collector electrode and the nozzle of the hydrogen gas burner, so that the rod-like element has a negative polarity to that of the collector electrode. As a result, positive ions caused by the burning and ionization of the separated substances collide with the rod-like element, thereby causing a propagation of electrons and distorting the linearity of the calibration characteristics. The grounds for this assumption will be explained in detail hereinafter.

SUMMARY OF THE INVENTION

It is an object of the present invention to provide a flame ionization detector used in the field of thin-layer chromatography, which is arranged so that it is possible to obtain calibration characteristics as a linear function, whereby an accurate quantitative analysis of chromatographically-separated substances can be carried out with a good reproducibility.

In accordance with the present invention, there is provided a flame ionization detector used in the field of thin-layer chromatography, which comprises: a gas burner connected to a hydrogen gas source to form a hydrogen flame at a nozzle thereof, a thin-layer chromatographic element which carries chromatographically-separated substances, and which is passed through the hydrogen flame to burn and ionize the separated substances; an electrode exposed to an ionized gas caused by the burning of the separated substances with the hydrogen flame; an electric source for applying a voltage between the hydrogen gas burner and the electrode so that the hydrogen gas burner has a positive polarity and the electrode has a negative polarity; a third electrode surrounding the negative electrode so that an amount of electricity with which the thin-layer chromatographic element is charged is reduced as much as possible; an amplifier for detecting and amplifying an electric current generated at the negative electrode by exposure to the ionized gas; and a recorder connected to the amplifier for recording an output therefrom as a chromatogram.

The third electrode may be held in an electrically floating condition, but preferably the third electrode is held at a higher electric potential than that of the negative electrode, since the amount of charged electricity of the thin-layer chromatographic element can be thus further reduced.

Preferably, the third electrode is arranged in a space between the hydrogen gas burner and the negative electrode and surrounding the negative electrode, to protect the determination from the affects of noise.

It should be noted that a feature of the thin-layer chromatography flame ionization detector according to the present invention is that the hydrogen gas burner has a positive polarity, the electrode has a negative polarity, and a third electrode surrounds the electrode having a negative polarity. This arrangement makes it possible for a calibration characteristic representing a relationship between an amount of each of the chromatographically-separated substances and an output value obtained from the amplifier at the amount thereof to be obtained as a linear function, as explained in detail hereinafter.

BRIEF DESCRIPTION OF THE DRAWINGS

The above and other objects, features and advantages of the present invention will be better understood from the following description, with reference to the accompanying drawings, in which:

FIG. 9 is a graph showing a voltage-output characteristic curve derived from an embodiment of the flame ionization detector according to the present invention, and representing a relationship between a voltage applied between a hydrogen gas burner and an electrode and an output value obtained from an amplifier at the applied voltage;

FIG. 10 is a graph showing a voltage-output characteristic curve derived from another embodiment of the flame ionization detector according to the present invention, and representing a relationship between a voltage applied between a hydrogen gas burner and an electrode and an output value obtained from an amplifier at the applied voltage;

DESCRIPTION OF THE PREFERRED EMBODIMENTS

Figure 1:
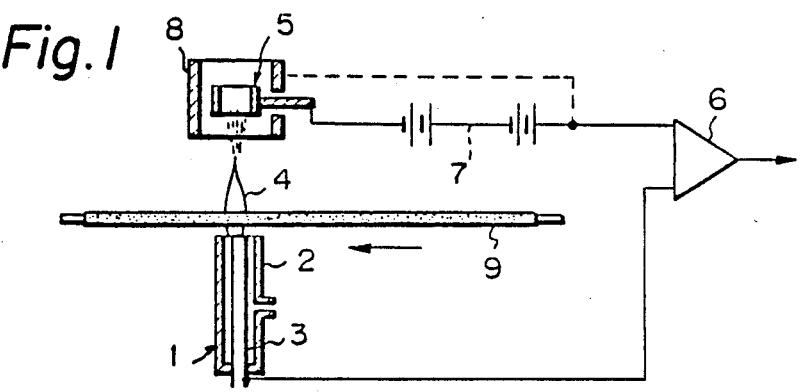
FIG. 1 is a schematic illustration of a flame ionization detector according to the present invention and used in the field of thin-layer chromatography.

FIG. 1 is a schematic illustration of a flame ionization detector, constructed according to the present invention, for a quantitative analysis of chromatographically-separated substances obtained from a sample solution in a thin-layer chromatography system. The flame ionization detector comprises a hydrogen gas burner 1 having an outer tubular member 2 for feeding air and an inner tubular member 3 for feeding hydrogen gas which is burned together with the fed air to form a hydrogen flame 4 at a nozzle of the hydrogen gas burner 1, as shown in FIG. 1. The flame ionization detector also comprises an annular electrode 5 disposed above a top of the hydrogen flame 4, an amplifier 6 connected to the annular electrode 5, and an electric source 7 provided between the annular electrode 5 and the amplifier 6. As apparent from FIG. 1, the annular electrode 5 is connected to a negative side of the electric source 7, to have a negative polarity, and the hydrogen gas burner 1 is connected to a positive side of the electric source 7 through the amplifier 6, to have a positive polarity. Preferably, the positive side of the electric source 7 is electrically grounded so that a signal can be stably input to the amplifier 6. According to the present invention, a third annular electrode 8 having a larger diameter than that of the negative electrode 5 is concentrically disposed and surrounds the negative electrode 5. The third annular electrode 8 may be held in an electrically floating condition, i.e., in an electrically insulated condition, or may be connected to the positive side of the electric source 7, as shown by a broken line in FIG. 1, so that the third electrode 8 is held at a higher electric potential than that of the negative electrode 5. A recorder (not shown) is connected to the amplifier 6 to record an output obtained therefrom as a chromatogram.

In FIG. 1, a thin-layer chromatographic element 9 may comprise, as mentioned above, a rod made of a refractory material such as silica glass and having a diameter of about 0.8 to 1.0 mm, and a thin layer formed on the rod by coating the surface thereof with an inorganic absorbent material such as silica gel, alumina, diatomite or the like. The thin-layer chromatographic element or rod-like element 9 carries chromatographically-separated substances formed by spotting a sample solution on the rod-like element and developing it along a length of the rod-like element with a developing solvent, as mentioned above. When the rod-like element 9 is gradually passed through the hydrogen flame 4 by a feeder device (not shown), which is per se well known in this field, the chromatographically-separated substances are burned and ionized by the hydrogen flame 4 to generate an ionized gas by which an ionization current is generated and which is detected by the amplifier 6, whereby a quantitative analysis of the separated substances can be carried out in substantially the same manner as in the flame ionization detector used in the field of gas chromatography. Note, that a calibration characteristic representing a relationship between an amount of each of the separated substances and an output value obtained from the amplifier at the amount thereof can be obtained as a linear function due to existence of the third electrode.

Figure 2:
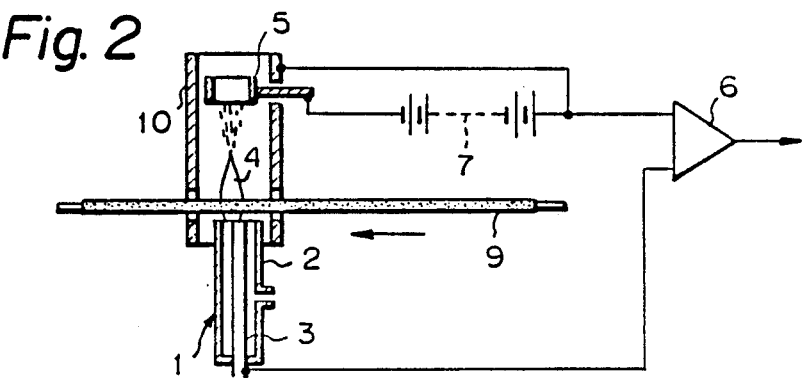
FIG. 2 is a schematic illustration of another embodiment of the flame ionization detector according to the present invention.

FIG. 2 shows a modification of the embodiment of FIG. 1. In FIG. 2, the same reference numerals as in FIG. 1 represent the same elements. In this modified embodiment, instead of the annular electrode 8, a cylindrical electrode 10 is used as the third electrode and is arranged in such a manner that a space between the hydrogen gas burner 1 and the negative electrode 5 is surrounded thereby, thus protecting the determination against the affects of noise.

In the embodiments of FIGS. 1 and 2, the negative electrode 5 may be replaced with a cylindrical ring- or disc-shaped electrode.

As discussed above, according to the present invention, because the negative electrode 5 is surrounded by the third electrode 8, 10, the calibration characteristics on the chromatographically-separated substances can be obtained as a linear function. The grounds therefor will be now explained on the basis of the research carried out by the inventor.

First, it will be shown that a calibration characteristic representing a relationship between an amount of each of the separated substances and an output value obtained from the amplifier at that amount is obtained as a curve such as an exponential function.

Figure 3:
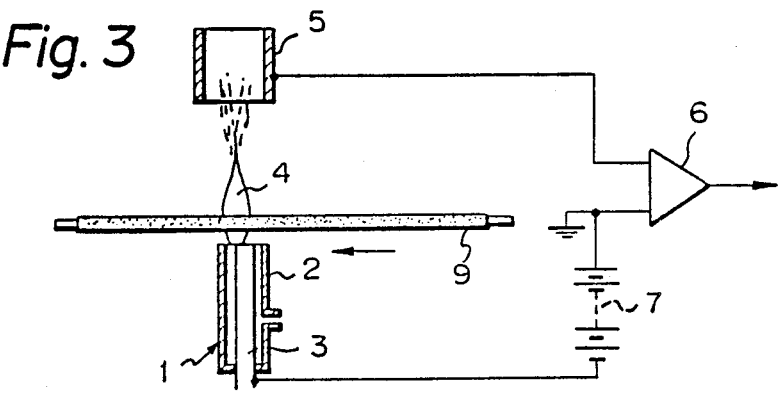
FIG. 3 is a schematic illustration of a known flame ionization detector used in the field of thin-layer chromatography.

FIG. 3 is a schematic illustration of a known flame ionization detector used in the field of thin-layer chromatography. In FIG. 3, the same reference numerals as in FIGS. 1 and 2 represent the same elements. This known flame ionization detector is substantially identical to that according to the present invention except that the third electrodes 8 and 10, which are a feature of the present invention, are not used, and that the polarities of the hydrogen gas burner 1 and the electrode 5 are reversed.

Figure 4:
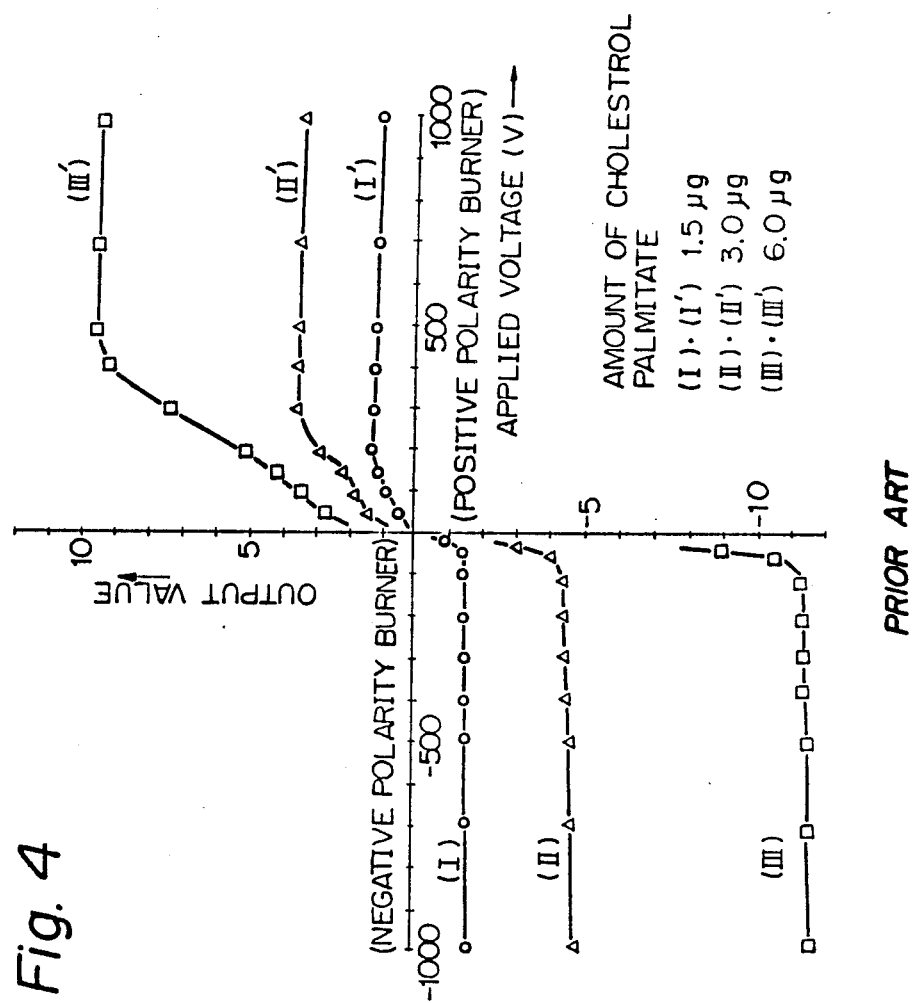
FIG. 4 is a graph showing a voltage-output characteristic curve derived from the known flame ionization detector and representing a relationship between a voltage applied between the hydrogen gas burner and the electrode and an output value obtained from the amplifier at the applied voltage.

FIG. 4 is a graph showing a voltage-output characteristic curve derived from the known flame ionization detector as shown in FIG. 3. In particular, the graph represents a relationship between a voltage applied between the hydrogen gas burner 1 and the positive electrode 5 and an output value from the amplifier 6 at the applied voltage when using a known amount of a sample substance (cholesterol palmitate) spotted on the thin-layer chromatographic element or the rod-like element 9 as a parameter. Concretely, the voltage-output characteristic curves I, II and III represent output values obtained from the amplifier 6 with respect t various values of the applied voltage when the rod-like elements on which 1.5 μg, 3.0 μg and 6.0 μg of cholesterol palmitate are spotted are passed through and burned by the hydrogen flame 4, respectively. Voltage-output characteristic curves I', II' and III' are similar to the voltage-output characteristic curves I, II and III, respectively, except that the polarities of the hydrogen gas burner 1 and the electrode 5 are reversed to each other.

As apparent from FIG. 4, when the hydrogen gas burner 1 has a negative polarity, a range which is less than about −100 Volt is obtained as a "saturated zone" in which the output values obtained from the amplifier 6 are not substantially affected by a fluctuation of the applied voltage. On the other hand, when the hydrogen gas burner has a positive polarity, such a saturated zone is in a range which is more than about 400 volts. Note, this is because the hydrogen gas burner 1 has a negative polarity in the known flame ionization detector. As seen from the voltage-output characteristic curves I, II and III, the output value of the amplifier 6 is not increased in proportion to an amount of the sample substance. For example, at −300 volts, which is conventionally used to determine a calibration characteristic, 1.5, 3.0, and 6.0 μg of cholesterol palmitate correspond to about 1.5, 4.5 and 11.5, respectively, which may be read from the graph as an output value of the amplifier 6, and thus there is no proportional relationship therebetween. In other words, it is impossible to obtain the calibration characteristic of the sample substance (cholesterol palmitate) as a linear function. The same is true for the voltage-output characteristic curves I', II' and III'.

As apparent from the foregoing, it can be assumed that the calibration characteristic cannot be gained as a linear function because the thin-layer chromatographic element or the rod-like element 9 is charged with electricity during the passage thereof through the hydrogen flame 4, due to existence of an electric field between the hydrogen gas burner 1 and the electrode 5. Accordingly, a measurement has been made of an electric potential of the rod-like element 9 during the passage thereof through the hydrogen flame 4. Requirements for such a measurement are as follows:

(a) The electrode 5 was spaced from the nozzle top of the hydrogen gas burner 1 by a distance of 15 mm, and while the rod-like element 9 was passed through the hydrogen flame 4, a space between the nozzle top and the rod-like element was maintained at 1 mm. This distance of 1 mm was selected so that chromatographically-separated substances which the rod-element carries can be completely burned with as small an amount of hydrogen gas as possible. For example, if the rod-like element 9 is spaced from the nozzle top by the distance of 3 mm, the separated substances cannot be completely burned. On the other hand, when the amount of hydrogen gas is increased to ensure a complete burning of the separated substances, the temperature of the hydrogen gas burner 1 and the electrode 5 is raised and the output value obtained from the amplifier 6 will include noise.

(b) The hydrogen gas burner 1 had a negative polarity and the electrode 5 a positive polarity, as in FIG. 3. A voltage of 300 volts was applied between the hydrogen gas burner 1 and the positive electrode 5.

(c) As the thin-layer chromatographic element 9, a rod-like element made of silica glass and coated with silica gel was used.

(d) A surface potential of the rod-like element was measured by an electrostatic potentiometer during the passage thereof through the hydrogen flame 4, and an output value obtained from the electrostatic potentiometer was recorded by a pen recorder.

Note, the requirements (a) and (c) hold true for the measurement as shown in FIG. 4.

Figure 5:
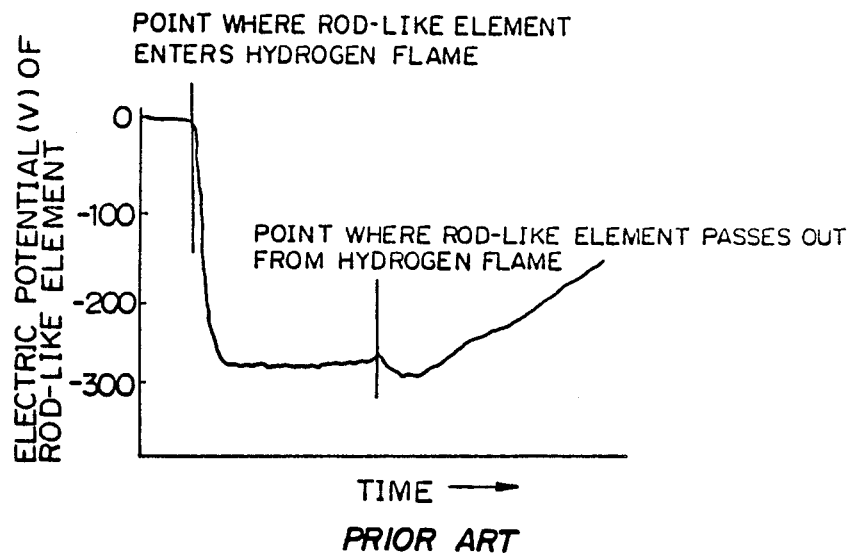
FIG. 5 is a graph showing an electric potential measured on a thin-layer chromatographic element when the element is passed through the hydrogen flame in the known flame ionization detector.

FIG. 5 shows the results of the measurement obtained from the pen recorder. It can be seen from FIG. 5 that the rod-like element has a potential of about −250 volts.

Figure 6:
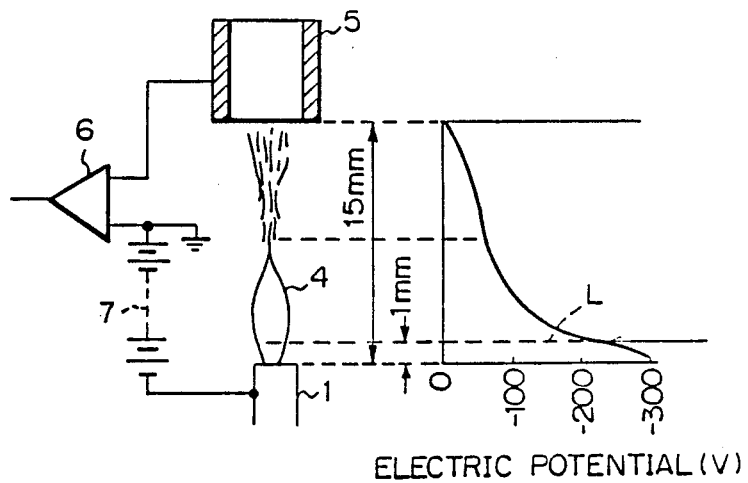
FIG. 6 is a schematic illustration of an electric potential distribution measured between the hydrogen gas burner and the electrode in the known flame ionization detector.

The inventor then measured an electric potential distribution between the hydrogen gas burner 1 and the positive electrode 5. The measurement was carried out by determining an electric potential of a needle probe of metal, which is shifted step by step between the hydrogen gas burner 1 and the positive electrode 5. The result of the measurement is schematically illustrated in FIG. 6. As apparent from FIG. 6, the potential distribution characteristic does not have a linear function due to existence of the hydrogen flame 4, but is curved as shown in FIG. 6. The potential of about −250 volts can be read from FIG. 6 at the level L, which is spaced from the nozzle top of the hydrogen gas burner 1 by the distance of 1 mm, that is, at which the rod-like element 9 passes through the hydrogen flame 4. This accords with the result of the measurement as shown in FIG. 5.

Therefore, in the known flame ionization detector, it was found that the rod-like element is charged with electricity and thus a potential difference between the rod-like element 9 and the positive electrode 5 becomes very high. In other words, the rod-like element or the thin-layer chromatographic element 9 lies in a high electric field zone. This is assumed to be the reason why the calibration characteristics become non-linear in the known flame ionization detector, as mentioned above, i.e., because the rod-like element 9 lies in the high electric field zone. In particular, when the chromatographically-separated substances carried by the rod-like element 9 are burned and ionized, the positive ions thus generated are accelerated and collide with the rod-like element 9, thereby causing a propagation of the electrons to break a linearity of the calibration characteristics.

In order to investigate the above assumption, the inventor carried out research into the variations of the relationship between an amount of a sample substance and an output value obtained from the amplifier 6 at the amount thereof, as a potential of the rod-like element 9 is made small. The process of above research by the inventor will be now described.

Figure 7:
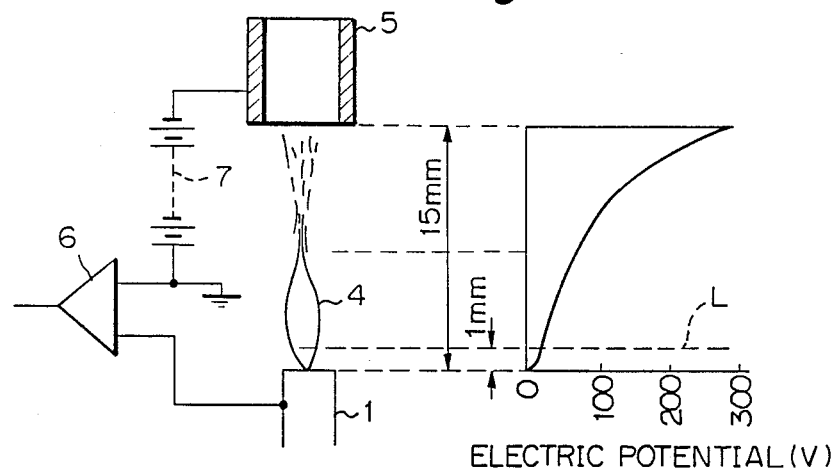
FIG. 7 is an illustration similar to FIG. 6, wherein the polarities of the hydrogen gas burner and the electrode are reversed.

First, to decrease the strength of the electric field at the side of the hydrogen gas burner 1 and thus reduce the potential of the rod-like element 9, the hydrogen gas burner 1 was given a positive polarity and the electrode 5 a negative polarity, and then an electric potential distribution therebetween was measured, in the same manner as in FIG. 6, when a voltage of 300 volts was applied therebetween. The results of the measurement are schematically illustrated in FIG. 7, similar to FIG. 6. From FIG. 7, a potential of about −25 volts can be read at the level L which is spaced from the nozzle tip of the hydrogen gas burner 1 by a distance of 1 mm.

Figure 8:
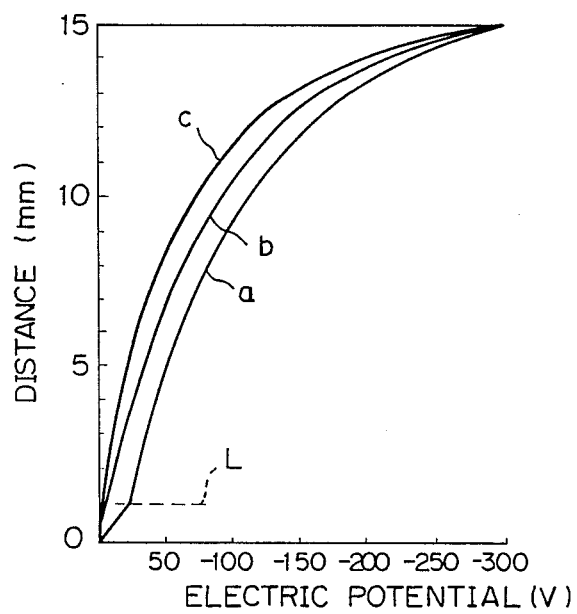
FIG. 8 is a schematic illustration, together with the electric potential distribution of FIG. 7, of an electric potential distribution measured between the hydrogen gas burner and the electrode in the flame ionization detector according to the present invention.

As already mentioned with reference to FIG. 4, it is impossible to obtain the calibration characteristics as a linear function only by giving the hydrogen gas burner 1 a positive polarity and the electrode 5 a negative polarity. Therefore, the inventor surrounded the negative electrode 5 with an electric conductor, based on the concept that the potential distribution of FIG. 7 could be shifted upwardly by causing an electrostatic induction between the negative electrode and the electric conductor, so that the electric field is strengthened at the side of the negative electrode 5 and weakened at the side of the hydrogen gas burner 1. The inventor carried out research into the variations in the potential distribution by using the electric conductor or the third electrode, as referred to in FIGS. 1 and 2, with the negative electrode 5. The results are shown in FIG. 8, in which a potential distribution a is the same as that in FIG. 7, a potential distribution b is obtained by holding the third electrode in the electrically floating condition, and a potential distribution c is obtained by maintaining the third electrode at a higher electrical potential than that of the negative electrode 5. As can be seen from FIG. 8, the potential values read from the potential distributions b and c at the level L are lower than those read from the potential distribution a at the same level. In the distribution b, the value is about −7 volts, and in the potential distribution c, the value is about −3 volts.

FIG. 9 shows voltage-output characteristic curves I′, II′ and III′ corresponding to the characteristic curves I′, II′ and III′ of FIG. 4, which were determined with respect to the potential distribution b in the same manner as in FIG. 4. As apparent from FIG. 9, each of the characteristic curves I″, II″ and III″ includes first and second saturated zones A and B, in which the output values obtained from the amplifier 6 are not substantially affected by fluctuations in the voltage applied between the hydrogen gas burner 1 and the negative electrode 5.

In the first saturated zone A, which corresponds to an applied voltage range of from about 200 volts to about 300 volts, it can be seen that the output value of the amplifier 6 is increased in proportion to the amount of the sample substance (cholesterol palmitate). For example, at 200 volts, 1.5, 3.0 and 6.0 μg of cholesterol palmitate correspond to about 1, 2, and 4, respectively, which may be read from the graph as an output value of the amplifier 6, and thus there is a proportional relationship therebetween. Accordingly, if a voltage within the range of from 200 to 300 volts is applied between the hydrogen gas burner 1 and the negative electrode 5, it is possible to obtain the calibration characteristic of the sample substance as a linear function.

In FIG. 9, a characteristic curve IV, designated by a broken line, represents a relationship between an electric potential of the rod-like element 9 and a voltage applied between the hydrogen gas burner 1 and the negative electrode 5. As apparent from the characteristic curve IV, when the potential of the rod-like element 9 is more than about −10 volts as an absolute value, the second saturated zone B appears in each of the characteristic curves I″, II″ and III″. In the second saturated zone B, there is no proportional relationship between the output value of the amplifier 6 and the amount of the sample substance, as in I′, II′ and III′ of FIG. 4.

FIG. 10 also shows voltage-output characteristic curves I‴, II‴ and III‴ corresponding to I′, II′ and III′ of FIG. 4, which were determined with respect to the potential distribution c in the same manner as in FIG. 4. As seen from FIG. 10, each of the characteristic curves I‴, II‴ and III‴ includes a saturated zone which corresponds to an applied voltage range of from 100 to 1,000 volts. In this saturated zone, it can be also seen that the output value of the amplifier 6 is increased in proportion to the amount of the sample substance (cholesterol palmitate). Accordingly, if a voltage within the range of from 100 to 1,000 volts is applied between the hydrogen gas burner 1 and the negative electrode 5, it is possible to obtain the calibration characteristic of the sample substance as a linear function.

Also, in FIG. 10, a characteristic curve IV′, designated by a broken line, represents a relationship between an electric potential of the rod-like element 9 and a voltage applied between the hydrogen gas burner 1 and the negative electrode 5. As apparent from the characteristic curve IV′, an applied voltage of 1,000 volts corresponds to a potential of about −10 volts at the rod-like element 9. Although not shown in FIG. 10, a second saturated zone appears in each of the characteristic curves I‴, II‴, and III‴ when the potential of the rod-like element 9 is more than about −10 volts as an absolute value (that is, when the applied voltage is more than 1,000 volts), but in the second saturated zone, there is not proportional relationship between the output value of the amplifier 6 and the amount of the sample substance.

In the measurement for obtaining the characteristic curves shown in FIGS. 9 and 10, the rod-like element having the coated thin layer of silica gel is used. But it is also possible to obtain characteristic curves similar to those shown in FIGS. 9 and 10 by using a rod-like element having a coated thin layer of alumina, diatomite or the like. It should be understood that the characteristic curves of FIGS. 9 and 10 are changeable according to the diameter of the rod-like element, the dimensions of the negative electrode and the third electrode or the like. In the measurement of the characteristic curves of FIGS. 9 and 10, as the negative electrode, an annular electrode having an inner diameter of 7 mm, an outer diameter of 9 mm, and a height of 4 mm, and as the third electrode, an annular electrode having an inner diameter of 14 mm, an outer diameter of 16 mm, and a height of 20 mm, are used.

In the embodiments of the present invention as mentioned above, when the third electrodes 8 and 10 are connected to the positive side of the electric source 7, the connection may be performed at any point between the amplifier 6 and the hydrogen gas burner 1. In this case, when the output of the electric source 7 is fluctuated, an electric current is generated due to an electrostatic connection between the negative electrode 8 and the third electrodes 8 and 10, and is then picked up by the amplifier 6. Accordingly, preferably, the third electrodes 8 and 10 are directly connected to the positive side of the electric source 7 without the intervention of the amplifier 6, as shown in FIGS. 1 and 2.

As already mentioned, in the embodiment as shown in FIG. 2, the determination can be protected from noise by using the cylindrical electrode 10 which surrounds the space between the hydrogen gas burner 1 and the negative electrode 5. In the embodiment as shown in FIG. 1, it has been actually observed that an output of the amplifier 6 is subjected to fluctuation when a human body is present in the vicinity of the hydrogen gas burner 1, but in this case, fluctuation of the output of the amplifier 6 can be prevented by using the cylindrical electrode 10.

In the embodiment of FIG. 2, although the cylindrical electrode 10 is connected to the positive side of the electric source 7, it may be held in the electrically floating condition as mentioned with reference to FIG. 1.

As apparent from the foregoing, in the thin-layer chromatography flame ionization detector according to the present invention, since it is possible to obtain a linear calibration characteristic representing an amount of each of chromatographically-separated substances and an output value obtained from an amplifier at the amounts thereof, an accurate quantitative analysis of the chromatographically-separated substances can be carried out with a good reproducibility.

To concretely show the advantages of the present invention in the quantitative analysis of chromatographically-separated substances, the flame ionization detector according to the present invention, as shown in FIG. 1, was compared with the known flame ionization detector shown in FIG. 3.

First, calibration characteristics have been prepared of substances to be quantitatively analyzed in both the detector according to the present invention and the known detector. The requirements for obtaining the calibration characteristics are as follows:

(a) As a liquid sample, toluene solutions of cholesterol ester (CE), triglyceride (TG), and free cholesterol (FC) were used. Note, the concentrations of these substances in each of the toluene solutions are known.

(b) As a thin-layer chromatographic element, a rod-like element comprising a rod made of silica glass and a thin layer of silica gel coated thereon was used. Each of the toluene solutions was dropped on the rod-like element in an amount of 1 μl, and was then developed and spread over 10 cm of the length of the rod-like element by a developing solution of 9:1 n-hexane:diethyl ether.

(c) The hydrogen gas burner was supplied with hydrogen gas at a rate of 160 ml/min and with air at a rate of 2,000 ml/min.

(d) A voltage of 300 volts was applied between the hydrogen gas burner and the negative electrode. The rod-like element was passed through the hydrogen flame at a rate of 4 mm/sec.

Figure 11:
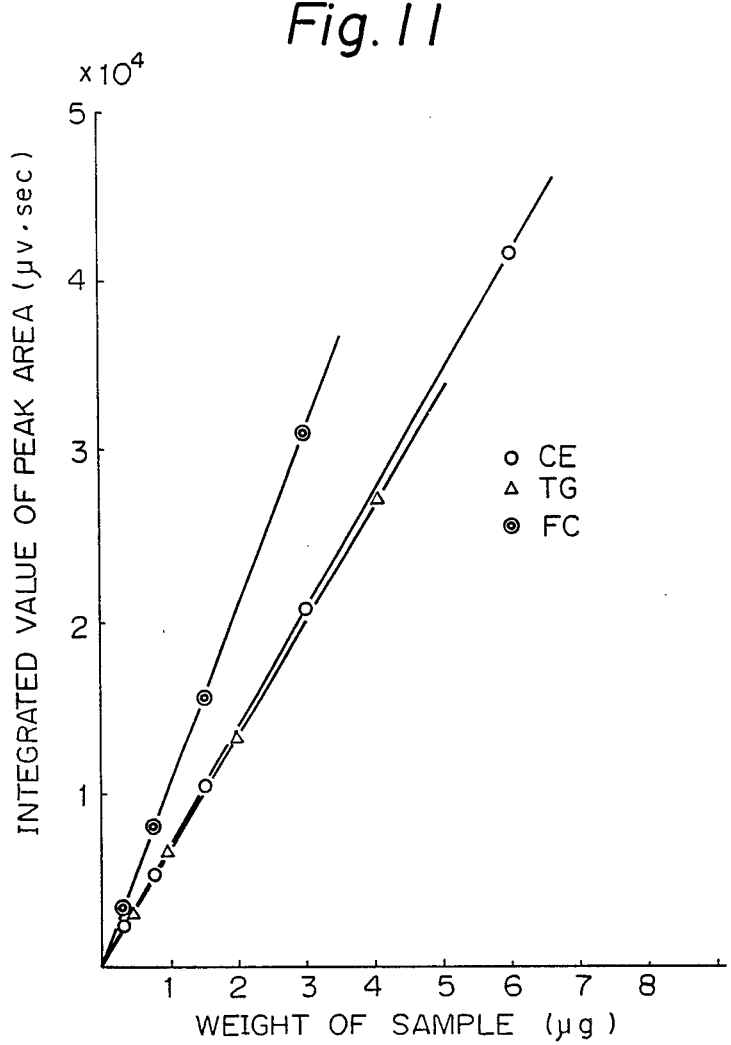
FIG. 11 is a graph showing, by way of example, calibration characteristics obtained in the flame ionization detector according to the present invention.
Figure 12:
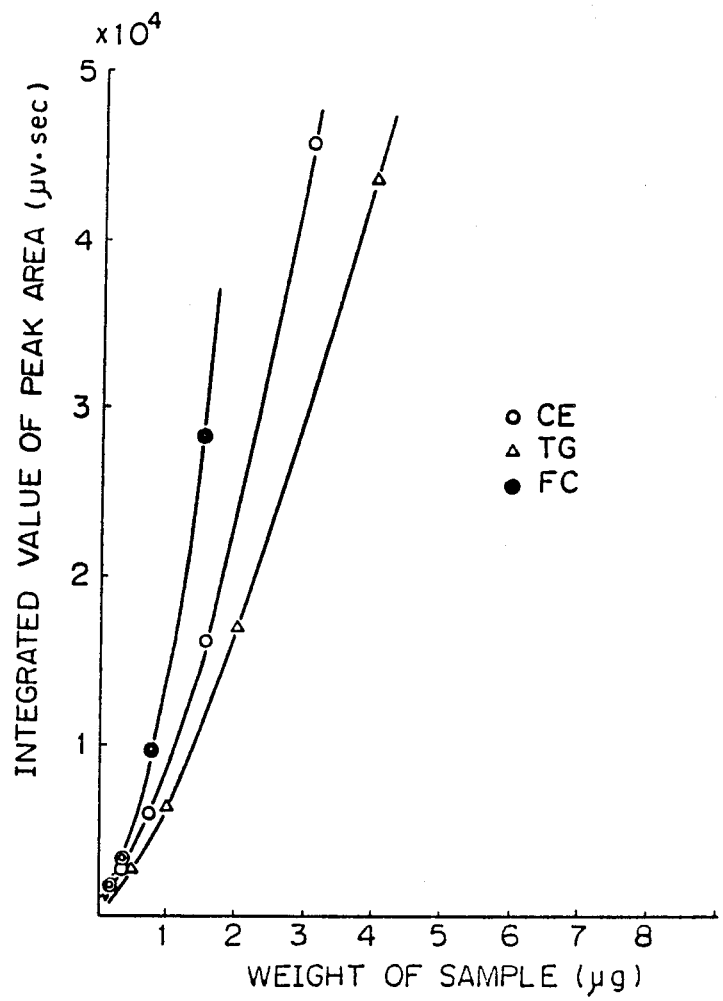
FIG. 12 is a graph showing, by way of example, calibration characteristics obtained in the known flame ionization detector.

The calibration characteristics obtained under the requirements mentioned above are shown in FIGS. 11 and 12. The calibration characteristics shown in FIG. 11 are derived from the detector according to the present invention (FIG. 1), and the calibration characteristics shown in FIG. 12 are derived from the known detector (FIG. 3). In FIGS. 11 and 12, symbols o, Δ, designate the calibration characteristics of cholesterol ester (CE), triglyceride (TG) and free cholesterol (FC), respectively. As seen from FIGS. 11 and 12, the calibration characteristics derived from the detector according to the present invention are obtained as a linear function, whereas the calibration characteristics derived from the known detector as obtained as a curve such as an exponential function. In FIGS. 11 and 12, the abscissa axis represents an amount (μg) of each of the separated substances, and the ordinate axis an integrated value (μv.sec) of an peak area of a chromatogram formed by recording output values obtained from the amplifier of the separated substances.

Accordingly, reproducibility of the detector according to the present invention as well as that of the known detector was tested by carrying out a quantitative analysis of known amounts of the substances, namely, cholesterol ester (CE), triglyceride (TG), and free cholesterol (FC) on the basis of the calibration characteristics of FIGS. 11 and 12. As a sample solution, a solution of 3.00 μg of cholesterol ester (CE), 4.00 μg of triglyceride (TG) and 1.50 μg of free cholesterol (FC) was used. The test was repeated five times. The results of the detector according to the present invention and the known detector are shown in TABLES I and II, respectively, below:

TABLE I

| | (INVENTION) | | |
|---|---|---|---|
| n | CE | TG | FC |
| 1 | 2.97 | 4.09 | 1.56 |
| 2 | 2.90 | 4.16 | 1.51 |
| 3 | 2.88 | 4.09 | 1.48 |
| 4 | 2.94 | 3.96 | 1.54 |
| 5 | 3.01 | 4.04 | 1.52 |
| $\bar{X}$ | 2.94 (3.00) | 4.07 (4.00) | 1.52 (1.50) |
| SD | 0.052 | 0.074 | 0.030 |
| CV | 1.8 | 1.8 | 2.0 |

TABLE II

| | (PRIOR ART) | | |
|---|---|---|---|
| n | CE | TG | FC |
| 1 | 3.41 | 3.91 | 1.36 |
| 2 | 3.19 | 3.87 | 1.44 |
| 3 | 3.25 | 3.82 | 1.51 |
| 4 | 3.37 | 4.04 | 1.58 |
| 5 | 3.09 | 3.72 | 1.40 |
| $\bar{X}$ | 3.26 (3.00) | 3.87 (4.00) | 1.46 (1.50) |
| SD | 0.131 | 0.118 | 0.088 |
| CV | 4.0 | 3.0 | 6.0 |

In TABLES I and II, n is a time of the test, calibrated values of cholesterol ester are shown in the CE column, calibrated values of triglyceride in the TG column, and calibrated values of free cholesterol in the FC column. Each of the calibrated values is read from the corresponding calibration characteristic on the basis of an integrated value of a peak area of the chromatogram which is formed by the output values of the amplifier. Also, in TABLES I and II, $\bar{E}$ is a mean value of the calibrated values shown in the corresponding column (A bracketed value is a true value thereof), SD is a standard deviation, and CV is a coefficient of variation. As apparent from TABLES I and II, in the detector according to the present invention, the reproducibility of the quantitative analysis can be considerably improved in the comparison with that of the known detector.

Furthermore, the detector according to the present invention was compared with the known detector in a daily test of reproducibility of a pattern analysis (Hydro Carbon-type Analysis) of heavy oil. In general, since a heavy oil comprises a complex mixture including various substances, it is impossible to chromatographically separate each of the substances from the complex mixture in the field of thin-layer chromatography, but in this case, the pattern analysis of the complex mixture is frequently carried out in the field of thin-layer chromatography. In the pattern analysis, the complex mixture is chromatographically separated into several groups, each of which comprises substances having similar chemical properties. Each of the groups is quantitatively evaluated by a percentage of a peak area thereof to a chromatogram area formed by output values obtained from the amplifier of the groups. Accordingly, the daily test of reproducibility of the pattern analysis is very significant.

In the daily test of reproducibility of the pattern analysis, the detector as shown in FIG. 1 (the third electrode 8 is connected to the positive side of the electric source 7) and the known detector as shown in FIG. 3 were also used. As a sample, a solution of 10 mg of heavy oil in 1 ml of dichloromethane was used. The sample was spotted on the thin-layer chromatographic element, i.e., the rod-like element, by an amount of 1 μl, and was then spread over a length of 10 cm of the element with a developing solvent of n-hexane. Thereafter, the rod-like element was dried at a room temperature. The sample was also spread over a length of 5 cm with a developing solvent of toluene, and was again dried at a room temperature. The sample was further spread over a length of 2 cm with a developing solvent of 95:5 dichloromethane:methanol. With this three-stage development, the sample was separated into four groups, i.e., saturate components, aromatic components, resin components, and asphaltene components.

The pattern analysis was carried out with each the two detectors (FIGS. 1 and 3) once a day for five days under the same operational requirements as in the quantitative analysis mentioned above. The results of the tests of the detector according to the present invention and the known detector are shown in TABLES III and IV, respectively, below:

TABLE III

| | (INVENTION) | | | |
|---|---|---|---|---|
| n | saturate components | aromatic components | resin components | asphaltene components |
| 1 | 33.9 | 51.8 | 8.0 | 6.3 |
| 2 | 33.7 | 51.6 | 8.1 | 6.6 |
| 3 | 33.6 | 51.9 | 8.2 | 6.3 |
| 4 | 34.2 | 51.0 | 8.5 | 6.3 |
| 5 | 34.0 | 51.8 | 8.1 | 6.1 |
| $\bar{X}$ | 33.9 | 51.6 | 8.2 | 6.3 |
| SD | 0.239 | 0.363 | 0.192 | 0.179 |
| CV | 0.7 | 0.7 | 2.3 | 2.8 |

TABLE IV

| | (PRIOR ART) | | | |
|---|---|---|---|---|
| n | saturate components | aromatic components | resin components | asphaltene components |
| 1 | 44.6 | 47.7 | 3.7 | 4.0 |
| 2 | 42.1 | 48.3 | 6.0 | 3.6 |
| 3 | 42.7 | 47.7 | 6.1 | 3.5 |
| 4 | 43.9 | 46.5 | 4.8 | 4.8 |
| 5 | 42.2 | 48.9 | 5.8 | 3.1 |
| $\bar{X}$ | 43.1 | 47.8 | 5.3 | 3.8 |
| SD | 1.102 | 0.890 | 1.023 | 0.644 |
| CV | 2.6 | 1.9 | 19.3 | 16.9 |

In TABLES III and IV, n is a time (day) of the test, and measured values of each of the separated components are shown in the corresponding column. Also, $\bar{X}$ is a mean value of the measured values shown in the corresponding column, SD is a standard deviation, and CV is a coefficient of variation.

As seen from TABLES III and IV, according to the present invention, it is possible to considerably reduce the coefficients of variation. Therefore, in the flame ionization detector according to the present invention, the reproducibility of the pattern analysis can be also considerably improved in comparison with that of the prior detector. Of course, this is derived from the fact that the amount of charged electricity of the thin-layer chromatographic element is reduced so as to prevent the propagation of the electrons, as discussed hereinbefore.

It should be understood that the form of the present invention herein described is a preferred example thereof and that various changes in the shape, size and arrangement of the parts may be made without departing from the spirit and scope of the present invention.

I claim:

1. A flame ionization detector used in thin-layer chromatography, comprising:

a gas burner connected to a means for providing a source of hydrogen gas to form a hydrogen flame at the nozzle of the burner, a thin-layer chromatographic element which carries chromatographically-separated substances and located such that it passes through the hydrogen flame to burn and ionize the separated substances;

a first electrode positioned such that it is exposed to an ionized gas caused by the burning of the separated substances with the hydrogen flame;

means defining an electric source said electric source means having a positive side and a negative side and being connected to said burner and to said first electrode for applying a voltage between said hydrogen gas burner and said first electrode whereby said hydrogen gas burner is given a positive polarity and said first electrode is given a negative polarity, whereby said burner forms a second electrode which functions as a positive electrode;

a third electrode surrounding said first electrode and relative to the first electrode, the third electrode being positioned and charged such that an amount of electricity with which said thin-layer chromatographic element is charged during its passage through the hydrogen flame is made to become as small as possible;

an amplifier for detecting and amplifying an electric current which is generated at said first electrode by exposure thereof to the ionized gas; and a recorder connected to said amplifier for recording an output obtained from said amplifier as a chromatogram.

2. The flame ionization detector according to claim 1, further comprising means for holding said third electrode in an electrically floating condition.

3. The flame ionization detector according to claim 1, wherein said third electrode is connected to the positive side of said electric source means, whereby said third electrode is held at a higher electric potential than that of said first electrode.

4. The flame ionization detector according to claim 1, wherein said third electrode is arranged so that the space between said first and second electrodes is surrounded by said third electrode.

* * * * *